Figure 1:
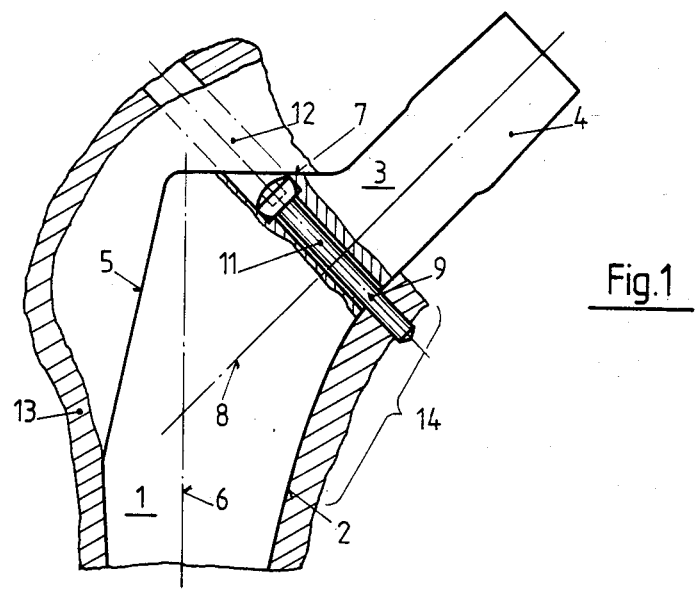

United States Patent [19]

Frey et al.

[11] Patent Number: 4,787,909
[45] Date of Patent: Nov. 29, 1988

[54] SHANK FOR A FEMUR HEAD PROSTHESIS

[75] Inventors: Otto Frey, Winterthur; Rudolf Koch, Berlingen, both of Switzerland

[73] Assignee: Sulzer Brothers Limited, Winterthur, Switzerland

[21] Appl. No.: 903,554

[22] Filed: Sep. 3, 1986

[30] Foreign Application Priority Data

Oct. 3, 1985 [CH] Switzerland ............... 4278/85-6

[51] Int. Cl.$^4$ ............................................. A61F 2/32
[52] U.S. Cl. ............................................. 623/23
[58] Field of Search ................... 623/16, 18, 22, 23

[56] References Cited

U.S. PATENT DOCUMENTS 3,995,323 12/1976 Shersher .................. 623/23
4,657,551 4/1987 Ecke ........................ 623/23

FOREIGN PATENT DOCUMENTS 2530254 1/1976 Fed. Rep. of Germany ........ 623/22
0501509 7/1979 U.S.S.R. ............................... 623/22
1442900 7/1976 United Kingdom .................. 623/23

Primary Examiner—Richard J. Apley
Assistant Examiner—David J. Isabella
Attorney, Agent, or Firm—Kenyon & Kenyon

[57] ABSTRACT

The collarless shank is provided with a bore for receiving a screw in order to permit securement of the proximal region of shank to the calcar arc of a femur bone. The bore is arranged in the proximal region and extends at least approximately perpendicularly to the medial arc of the shank as well as perpendicularly to the prosthesis neck axis. The screw may be passed through a continuous bore into the calcar arc or may be passed through the calcar arc into threaded engagement in a blind bore of the shank.

7 Claims, 1 Drawing Sheet

SHANK FOR A FEMUR HEAD PROSTHESIS

This invention relates to a shank for a femur head prosthesis.

Heretofore, various types of shanks have been employed with a femur head prosthesis. Usually, the shanks have been constructed so as to be firmly wedged in a bone in a distal region while changing over medially via an arc into a prosthesis neck, for example as described in U.S. Pat. No. 4,404,693. However, if such shanks are made without a collar, it has been found that micromovements occur in the region of the calcar arc of the bone which lead to bone degradation and, ultimately, losening of the prosthesis. These micromovements are caused by pulsating pressure forces which occur, with the distal end "clamped in", due to the elasticity of the shank as a result of the bending movements caused by load applications and load relief at the joint head. In addition, for a cement-free anchoring, the problem of primary fixation in the proximal shank region arises.

Accordingly, it is an object of the invention to preclude micromovements at the calcar arc in the case of a collarless femur head prosthesis.

It is another object of the invention to preclude micromovements of a shank at a calcar region which has been fixed at a distal end.

It is another object of the invention to reduce the detrimental effects caused by pulsating pressure forces on an implanted shank of a femur head prosthesis.

Briefly, the invention provides a collarless shank for a femur head prosthesis having a proximal region and means for securing the proximal region to a calcar arc of a bone.

The shank also includes a medial arc in the proximal region, a prosthesis neck which extends from the medial arc and a bore in the proximal region which is disposed at least nearly perpendicularly on the medial arc in order to receive a screw for securing the proximal region of the shank to the calcar arc.

In one embodiment, the bore extends through the proximal region while the screw passes through the bore and is threaded into the calcar arc. In this case, use is made of a self-threading screw.

In another embodiment, the bore is a threaded blind bore while the screw passes through the calcar arc into threaded engagement with the proximal region.

Use of the screw permits a primary fixation of the shank in the proximal region immediately with implantation. Moreover, the shank and bone are firmly joined together in the proximal region so that pulsating pressure forces cannot act on the bone.

In order to facilitate correct "setting" of the "channels" necessary in the bone, i.e. so that the channels match the bore in the shank, it has been proven to be effective if the bore extends at least approximately perpendicular to the axis of the prosthesis neck.

The invention also provides a method of implanting a collarless shank for a femur head prosthesis in a surgically prepared bone in a manner to avoid pulsating pressure forces. To this end, the method includes the steps of implanting a distal end of the shank in the bone; positioning a medial arc of the prosthesis against the calcar arc of the bone and thereafter securing a proximal region of the implant to the calcar arc in order to eliminate micromovements due to subsequently applied pulsating pressure forces.

Figure 2:
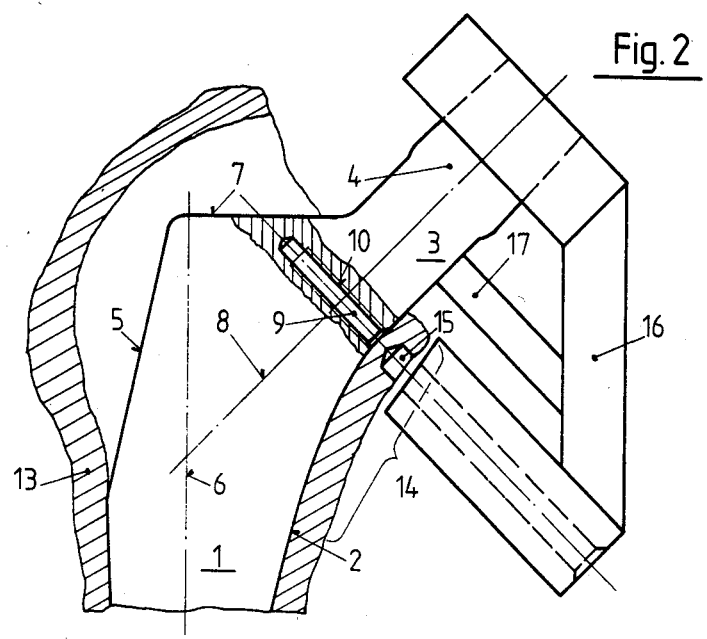

These and other objects and advantages of the invention will become more apparent from the following detailed description taken in conjunction with the accompanying drawings wherein:

FIG. 1 illustrates a portion of a femur head prosthesis which has been secured to a calcar arc in accordance with the invention; and FIG. 2 illustrates a modified shank secured to a calcar arc in accordance with the invention.

Referring to FIG. 1 a collarless shank 1 for a femur head prosthesis, which is shown only in the proximal portion, has a cross-section which may be of blade-like shape, that is, in the form of a relatively narrow rectangle. Alternatively, the shank may have any other suitable cross-sectional form, as for example, cuboid, prismatic or rounded. As shown, the shank 1 has a proximal region which is disposed along a longitudinal axis 6, a medial arc 2 in the proximal region and a prosthesis neck 3 which extends from a proximal region on a second axis 8 inclined to the longitudinal axis 6. The shank 1 is formed without a collar and the neck 3 is adapted to receive a prosthesis head (not shown) on a conical pin 4 as is known.

The lateral wall of the shank 1 widens at first from the distal end to the proximal region in a conical manner before terminating in an inclined wall 5 which extends toward the longitudinal axis 6. The inclined wall 5, in turn, extends inwardly, as viewed, to terminate in a horizontal shoulder 7 which forms a transition to the prosthesis neck 3.

As indicated in FIG. 1, when the shank 1 is properly seated in the bone 13, the medial arc 2 is positioned against the calcar arc 14 of the bone 13.

A means is also provided for securing the proximal region of the shank 1 to the calcar arc 14. As indicated, this means includes a screw 11 which passes through a bore 9 in the proximal region of the shank 1 adjacent to the neck 3 and which is threaded into the calcar arc 14. In this regard, the bore 9 is a continuous bore through the shank 1 and is disposed at least nearly perpendicular to the surface of the medial arc 2 and also perpendicular to the axis 8 of the prosthesis neck 3. The screw 11 is a self-threading bone screw so as to be threaded into the calcar arc 14. In addition, a surgically pre-drilled channel 12 is provided in the bone 13 from lateral/proximal obliquely to medial/distal in order to permit passage of the screw 11 into the bore 9 and calcar arc 14.

In use, after the shank 1 has been implanted so that the distal end is fixed in place, the screw 11 is passed through the pre-drilled channel 12 and the bone 13 into the bore 9. Thereafter, the screw 11 is threaded into and through the calcar bone 14 as indicated in FIG. 1 in order to secure the proximal region of the shank 1 to the calcar arc 14.

Referring to FIG. 2, wherein like reference characters indicate like parts above, the bore 9 in the proximal region of the shank 1 may be in the form of a blind bore 9 with an internal thread 10. In this case, the screw (not shown) may be passed through an opening 15 in the cortex of the calcar arc 14 into threaded engagement with the thread 10 of the bore 9. In this embodiment, formation of a pre-drilled channel in the trochanteric region of the bone 13 can be omitted.

The setting of the opening 15 in the correct location of the cortex of the calcar arc 14 can be made possible by a template 16. As indicated in FIG. 2 the template 16 can be placed on the conical pin 4 of the shank with an exact fit. In addition to determining the distance between the end of the pin 4 and the bore 9 along the prosthesis neck axis 8, the template also establishes the "correct pitch" relative to the prosthesis neck axis 8 required for the bore 15 to be aligned with the bore 9. Further, by means of a support 17 abutting laterally against the prosthesis neck 3, the position of the opening 15 in the anterior/posterior direction can be made beforeformingly opening 15. Of note, a similar template (not shown) may be used to form the channel 12 for the embodiment illustrated in FIG. 1.

The invention thus provides a relatively simple technique for securing a shank of a femur head prosthesis in a proximal region to eliminate problems caused by pulsating pressure forces. Further, the technique may be employed during implantation of the shank.

The invention also provides for an improved primary fixation of a shank in a surgically prepared femur bone.

What is claimed is:

1. In combination
a collarless shank for a femur head prosthesis having a proximal region; a medial arc in said proximal region for positioning against a calcar arc of a femur; a prosthesis neck extending from said medial arc; and an unthreaded bore in said proximal region disposed at least nearly perpendicularly of said medial arc and perpendicular to said neck; and
a screw passing through said bore in unthreaded relation for threading into the calcar arc to secure said proximal region to and against said calcar arc.

2. In combination
a collarless shank for a femur head prosthesis having a proximal region disposed along a longitudinal axis, a medial arc in said proximal region for positioning against a calcar arc of a femur a prosthesis neck extending from said proximal region on a second axis inclined to said longitudinal axis and a bore in said proximal region perpendicular of said medial arc; and
a threaded screw for securing said proximal region to a calcar arc of a bore, said screw passing through one of said bore and said calcar arc in unthreaded relation and passing through the other of said bone and calcar arc in threaded relation.

3. The combination as set forth in claim 2 wherein said bore is perpendicular to said second axis.

4. The combination as set forth in claim 2 wherein said bore is threaded to receive said screw.

5. A method of implanting a collarless shank for a femur head prosthesis in a surgically prepared bone comprising the steps of
implanting a distal end of the shank in the bone;
positioning a medial arc of the prosthesis against the calcar arc of the bone and a bore disposed perpendicularly of said medial arc; and
thereafter passing a screw in unthreaded relation through one of said bore in the proximal region of the implant and said calcar arc and into threaded relation with the other of the proximal region and calcar arc to secure the proximal region of the implant to said calcar arc to eliminate micromovements of the prosthesis due to subsequently applied pulsating pressure forces.

6. A method as set forth in claim 5 where the screw is threaded perpendicularly through the calcar arc into an unthreaded bore in the proximal region of the implant.

7. A method as set forth in claim 5 wherein a headed screw is passed through an unthreaded bore in the proximal region of the implant and threaded into the calcar arc.

* * * * *

UNITED STATES PATENT AND TRADEMARK OFFICE
CERTIFICATE OF CORRECTION

PATENT NO. : 4,787,909

DATED : November 29, 1988

INVENTOR(S) : OTTO FREY and RUDOLF KOCH

It is certified that error appears in the above-identified patent and that said Letters Patent is hereby corrected as shown below:

```
Column 3, line 8 "formingly" should be -forming the-
Column 4, line 4 "bore" should be -bone-
Column 4, line 6 "bone" should be -bore-
```

Signed and Sealed this

Fifteenth Day of August, 1989

Attest:

DONALD J. QUIGG

Attesting Officer

Commissioner of Patents and Trademarks